United States Patent [19]
Dussault

[11] Patent Number: 5,421,189
[45] Date of Patent: Jun. 6, 1995

[54] ELECTRICAL CONNECTION SYSTEM FOR ELECTROCHEMICAL SENSORS

[75] Inventor: Richard A. Dussault, No. Attleboro, Mass.

[73] Assignee: Ciba Corning Diagnostics Corp., Medfield, Mass.

[21] Appl. No.: 184,315

[22] Filed: Jan. 21, 1994

[51] Int. Cl.6 .................. H01R 29/00; H01R 13/703; G01N 27/00
[52] U.S. Cl. ..................... 73/19.1; 439/188
[58] Field of Search .................. 73/19.1, 19.01, 31.05; 371/23; 439/188; 200/43.05, 61.03, 61.04, DIG. 16

[56] References Cited

U.S. PATENT DOCUMENTS

| | | | |
|---|---|---|---|
| 3,946,390 | 3/1976 | Alexander et al. | 343/702 |
| 4,179,178 | 12/1979 | Bachman et al. | 339/111 |
| 4,358,135 | 11/1982 | Tsuge et al. | 280/806 |
| 4,367,907 | 1/1983 | Buck | 439/188 |
| 4,438,303 | 3/1984 | Astier | 200/51.1 |
| 4,568,919 | 2/1986 | Muggli et al. | 340/518 |
| 4,633,048 | 12/1986 | Komatsu | 200/51.1 |
| 4,904,196 | 2/1990 | Sueyoshi et al. | 439/188 |
| 4,971,569 | 11/1990 | Gooch et al. | 439/188 |
| 5,007,851 | 4/1991 | Matsumoto | 439/188 |
| 5,030,122 | 7/1991 | Birch et al. | 439/188 |
| 5,030,123 | 7/1991 | Silver | 439/188 |
| 5,052,940 | 10/1991 | Bengal | 439/188 |
| 5,064,973 | 11/1991 | Zinn et al. | 200/51.1 |
| 5,074,801 | 12/1991 | Siemon | 439/188 |
| 5,090,915 | 2/1992 | Moulton | 439/188 |
| 5,147,992 | 9/1992 | Eriksen et al. | 200/51.1 |

Primary Examiner—Hezron E. Williams
Assistant Examiner—Michael J. Brock
Attorney, Agent, or Firm—Arthur S. Morgenstern; Nicholas I. Slepchuk, Jr.; Judith A. Roesler

[57] ABSTRACT

An electrochemical/gas analyzer providing a rugged contact system for removable sensors capable of withstanding inexpert sensor insertion or removal, providing protection for high impedance input electronics against electrostatic discharge (ESD) damage, and providing automatic connection to diagnostic circuitry upon sensor removal has been developed. The contact system includes a plurality of stamped contacts electrically connecting a diagnostic circuit, including a source of diagnostic signals and a ground path, to analyzer signal processing circuitry. Removal of a sensor from this system electrically connects the sensor signal processing electronics to the diagnostic circuit. Insertion of the sensor interrupts electrical connection between the diagnostic circuit and the stamped contact, which connects the sensor terminals to the signal processing circuitry.

21 Claims, 9 Drawing Sheets

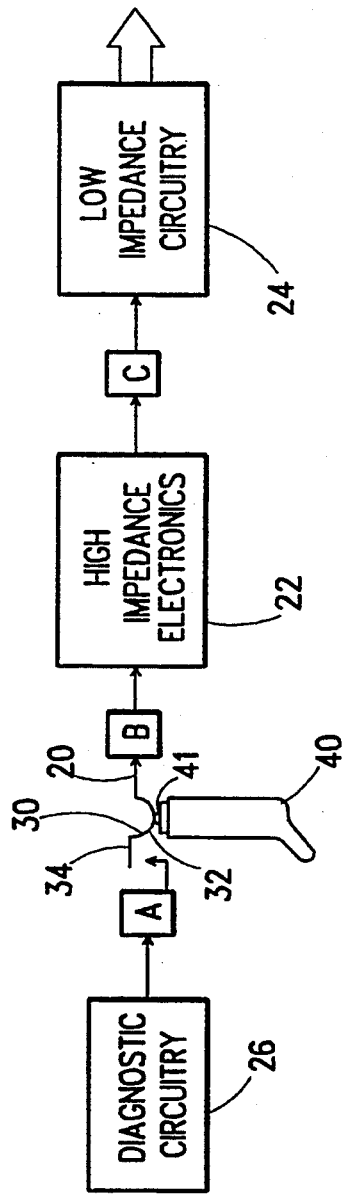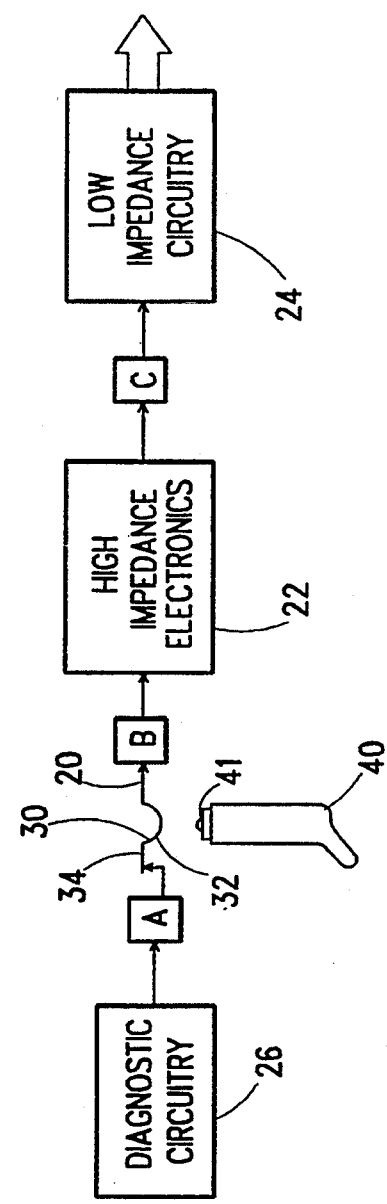

ELECTRICAL CONNECTION SYSTEM FOR ELECTROCHEMICAL SENSORS

FIELD OF THE INVENTION

This invention relates to the field of electrochemical/gas analyzers, and more particularly to the implementation of diagnostics in electrochemical/gas analyzers.

BACKGROUND OF THE INVENTION

Electrochemical/gas analysis systems are known having sensor units for specific analysis tests selectively installable in a multi-channel analysis system. Electrical connections are made between the individual sensor contacts and contacts on the analysis system.

Prior sensor electrode to analyzer system contacts were extremely delicate and required time-consuming and expensive hand assembly. Careless insertion or removal of sensors into these connectors could easily result in connector damage. In addition to low insertion-removal cycle lifespans, these connectors frequently provided less than optimal sensor to system signal reliability.

A major problem which prior art analysis systems fail to address is the ease with which front-end electronics with input impedances of several hundred million ohms can be damaged by electrostatic discharge (ESD) which occasionally occurs on insertion of static charged sensors. Some sensors have plastic bodies prone to static charge build-up, particularly when employed in low humidity environments. A charged sensor brought into contact with an analysis system contact can apply built-up potential to the high impedance, front-end electronics, thereby damaging them.

There is a need for simple and accurate diagnostic testing of analysis system electronics including high impedance front-end pre-amplifier circuitry and low impedance back-end signal processing circuitry.

In order to test these elements, one prior art gas analysis system provides a diagnostic tool which may be referred to as an electrode simulator. In this prior art analysis system, it is necessary to remove all of the sensors from the system when it is suspected that either a sensor or one channel of a multi-channel system is malfunctioning. The sensor simulator, which is battery powered, is installed in place of the sensors and is electrically connected to the sensor contacts to provide test signals to the analysis system through the same contacts that connect the front-end and back-end electronics.

Because all electrodes must be removed in order to install the electrode simulator, time is consumed and sensors which are not suspect are thereby subject to foreign matter introduction, damage or loss. Further, increased removal-insertion cycling decreases the life expectancy both of the sensor and system contacts. Finally, a discrete piece of test equipment such as the electrode simulator is expensive to manufacture in small quantities, requires separate maintenance, and must be located and transported to the analyzer system site by service personnel.

Another prior art approach to providing enhanced testing of an electrochemical/gas analyzer system involves providing reed relays to selectively insert a test signal to the high impedance front-end electronics in place of a sensor signal. Contact testing cannot be achieved and implementing reed relays requires additional space proximate the front-end electronics.

SUMMARY OF THE INVENTION

An electrochemical/gas analyzer providing a rugged contact system for removable sensors capable of withstanding inexpert sensor insertion or removal, providing protection for high impedance input electronics against electrostatic discharge (ESD) damage, and providing automatic connection of sensor front end electronics to diagnostics upon sensor removal has been invented.

The present electrochemical/gas analyzer provides resilient electrical contacts as elongated contacting stampings captured between a printed circuit board and a sensor mating housing having flex in response to insertion or removal of a sensor. Alignment of the sensor with respect to an associated contact captured between the housing and printed circuit board is not critical. The contact stamping is easily fabricated according to known stamping methods, and is capable of simple, fully automated installation and retention between the printed circuit board and housing of the present analyzer.

In the assembled printed circuit board and housing, each contact stamping has a remote portion which has a spring loaded connection to a printed circuit board contact that leads to ground or diagnostics. During sensor installation, each sensor contact makes initial physical and electrical contact with an arcuate (curved) portion of the stamping while the remote portion remains in contact with the printed circuit board contact. As a result, diagnostic circuitry, which may be disposed on the circuit board, is connected through a remote portion terminus to the sensor, and further to the signal processing electronics. The diagnostic circuitry may include a path to electrical ground through an output of a voltage generator, or may provide a path to ground through a switch. In either configuration, static potential built up on the sensor body is drained to ground and the high impedance front-end electronics are protected from ESD damage.

When the sensor is fully installed, the remote portion of the contact stamping is urged off the printed circuit board, thus interrupting electrical connection with the diagnostic circuitry and leaving the sensor connected to the front end.

By merely removing a single sensor from the analyzer, the remote portion electrically connects the diagnostic circuitry to the signal processing electronics and allows for fully automated diagnostic testing of the contact, of the high impedance front-end electronics, and of the low impedance back-end circuitry while other sensors remain fully installed.

BRIEF DESCRIPTION OF THE DRAWINGS

These and other features, objects and benefits of the present invention are more fully set forth below in the detailed description of an illustrative embodiment and in the accompanying drawing of which:

FIG. 1a is a schematic representation of an electrochemical/gas analyzer according to the present invention having a sensor installed therein;

FIG. 1b is the schematic representation of FIG. 1a in which the sensor is shown removed;

FIG. 2 is a perspective view of a measurement module portion of the electrochemical/gas analyzer of FIG. 1a;

DETAILED DESCRIPTION

Figure 2:
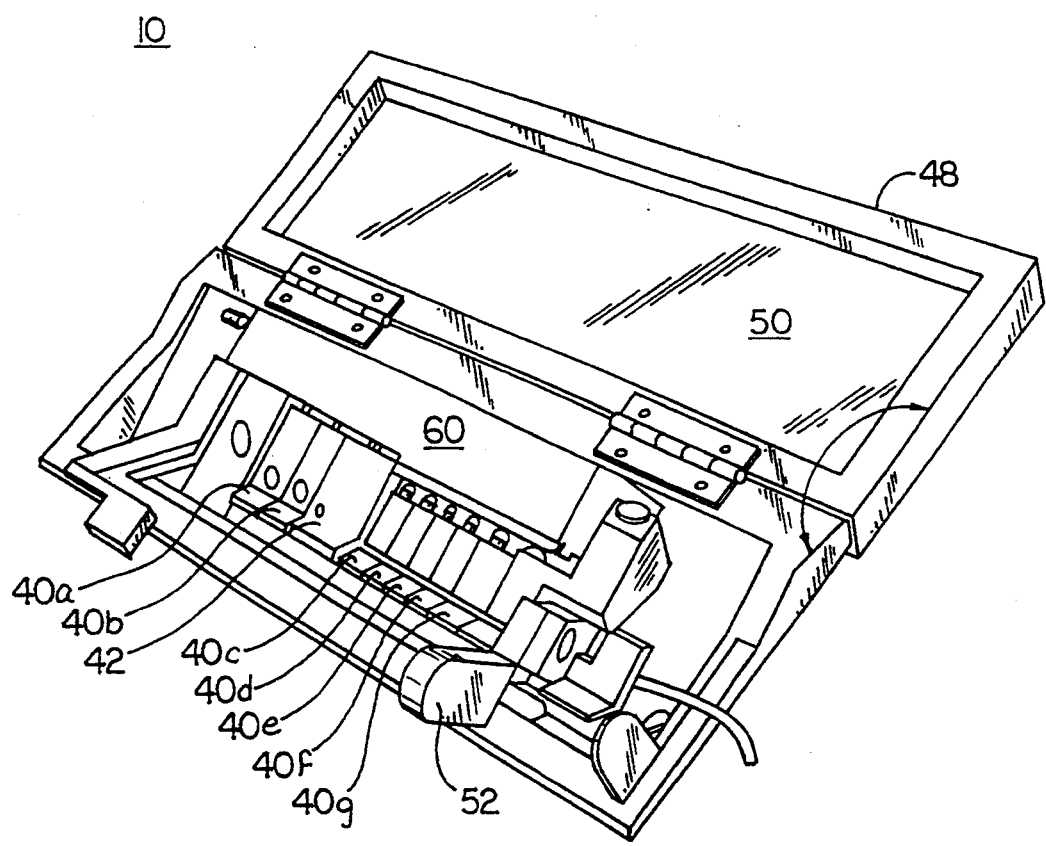

A new and novel electrochemical/gas analyzer configuration providing an analyzer capable of executing comprehensive diagnostic testing, and of providing electrostatic discharge damage protection for high impedance front-end electronics, is disclosed.

With reference to FIG. 1a, improved diagnostic testing over prior art analyzers is enabled in the present invention by providing test signals at a point A such that contact stampings 20, high impedance front-end electronics 22, and low impedance back-end signal processing circuitry 24 are all tested. Test signals can be provided from diagnostic circuitry 26 in the form of a discrete DC voltage or current, a repetitive series of DC step voltages or currents (simulating a sensor response output signal), though other variations may be used. In one embodiment, the source of test signals can be a digital-to-analog converter (DAC). Other embodiments can utilize the outputs of DC voltage or current sources.

To enable the provision of test signals at the point A for testing as described, the contact stampings 20 of the present invention having a remote portion 30 are advantageously utilized. The remote portion 30 is made up of an arcuate portion 32, which extends through a housing aperture and against which one or more sensor contacts 41 of an installed sensor 40 presses, and a remote portion terminus 34. In FIG. 1a, such a sensor 40 is installed within the analyzer and sensor contact 41 is electrically connected with the contact stamping 20, thus lifting the arcuate portion 32. This in turn raises remote portion terminus 34, interrupting electrical connection between the diagnostic circuitry 26 and the rest of the analyzer. In FIG. 1b, the sensor 40 is removed, thus allowing the remote portion terminus 34 to electrically connect the diagnostic circuitry 26 to the remainder of the analyzer.

Each contact 20 as described herein is manufactured from resilient materials and undergoes limited motion as a result of installation and removal of a sensor 40. As a result, a rugged contact stamping 20 is provided, capable of withstanding improper sensor 40 insertion and having a high insertion-removal life cycle relative to prior art sensor connector systems.

Another important benefit is provided through the use of the contact stamping remote portion 30 as described. Sensors 40 employed in analogous electrochemical/gas analyzers typically employ plastic as shell material, thus making the sensors 40 susceptible to static potential build-up. When sensors 40 are first installed within these analyzers, a built-up electrostatic charge can discharge into the high impedance, front-end electronics 22 which are prone to electrostatic discharge (ESD) damage. However, in the present invention, the diagnostic circuitry 26 provides a low impedance or direct path to electrical ground in addition to providing the test signals. Thus, when the sensor contact 41 of a statically charged sensor 40 is initially brought into contact with the contact stamping remote portion 30, the static potential is dissipated through the diagnostic circuitry 26 to ground.

With reference now to FIG. 2, a measurement module for the electrochemical/gas analyzer according to the present invention, including the remote portion 30, is illustrated. Typically, the analyzer of the present invention will simultaneously test several aspects of a medium, such as blood, introduced through consecutively disposed sensors 40a–40g. Also provided within the measurement module is at least one component 42 (only one such component is shown within this figure) which provides an electrical connection to the measured medium and a sensor to measure the temperature of the medium being tested.

To gain access to the sensors 40a–40g installed in the analyzer front panel 10, a thermally insulating cover 48 is raised as shown. The cover 48 preferably has an opaque window 50 of a thermally insulating material such as glass or plastic. With the cover raised, installed sensors 40a–40g are exposed. By urging a compressive member 52 away from the sensors 40a–40g (to the right in FIG. 2), any one sensor 40 can be removed from an analyzer housing 60, the latter being better illustrated in FIGS. 3 and 4.

A source 51 for the medium under test and a receptacle 53 into which the tested material flows are illustrated in FIG. 2 schematically and are known in the art. The source 51 can be substituted with a number of reference materials, depending on which aspects of the medium are being analyzed. Such materials may include reference gases, calibration materials, etc.

Figure 3:
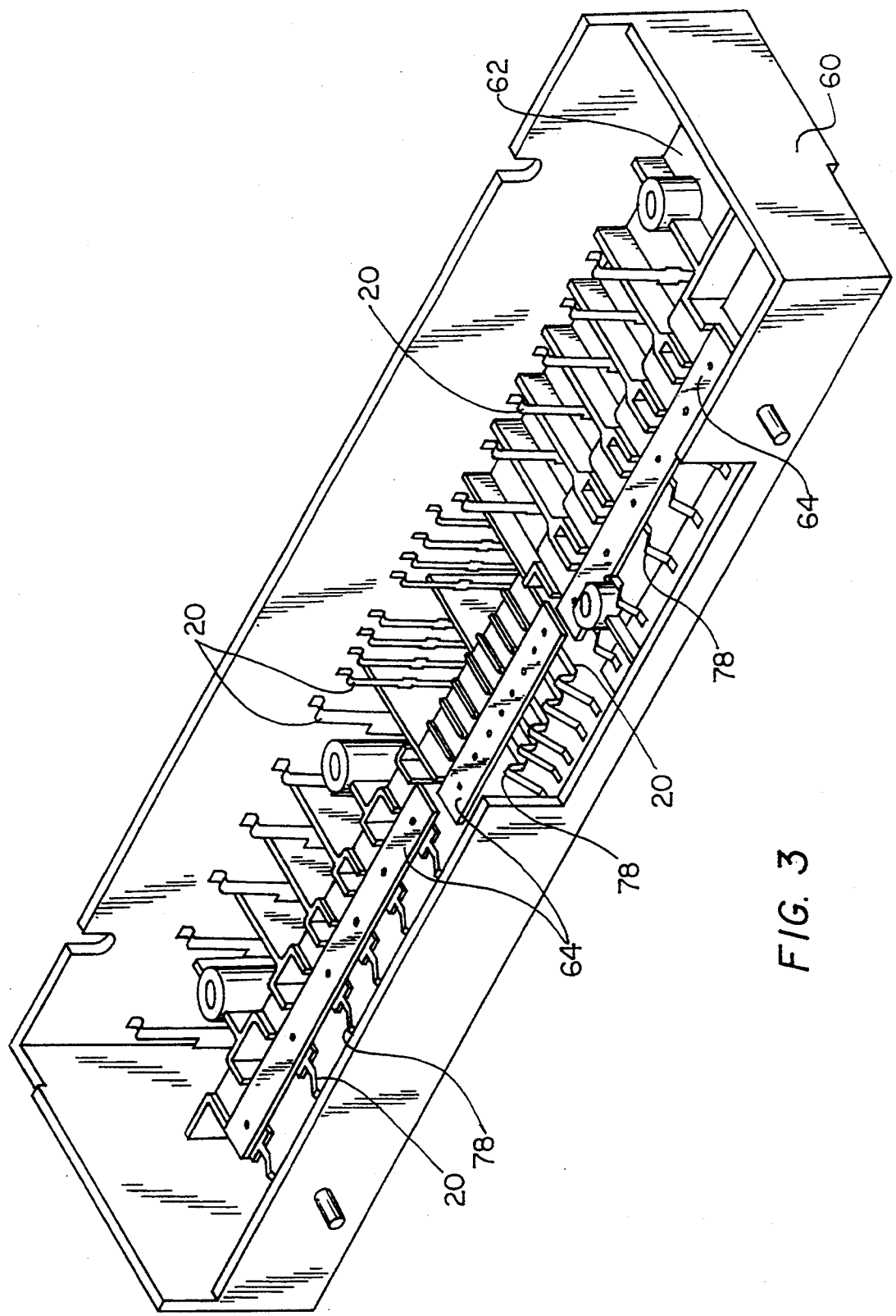
FIG. 3 is a perspective view of an interior region of a housing of the analyzer of FIG. 2.

The interior of the measurement housing has a contact housing 60 illustrated in FIG. 3. Contact stampings 20 are secured on a stamping retention face 62 by positioning retention members 64 across the contact stampings 20, then ultrasonically welding the retention members 64 to the stamping retention face 62. Other means for adhering the retention members 64 to the retention face 62 known in the art may be employed such as gluing, snap-fitting, and using screws or the like.

Figure 4:
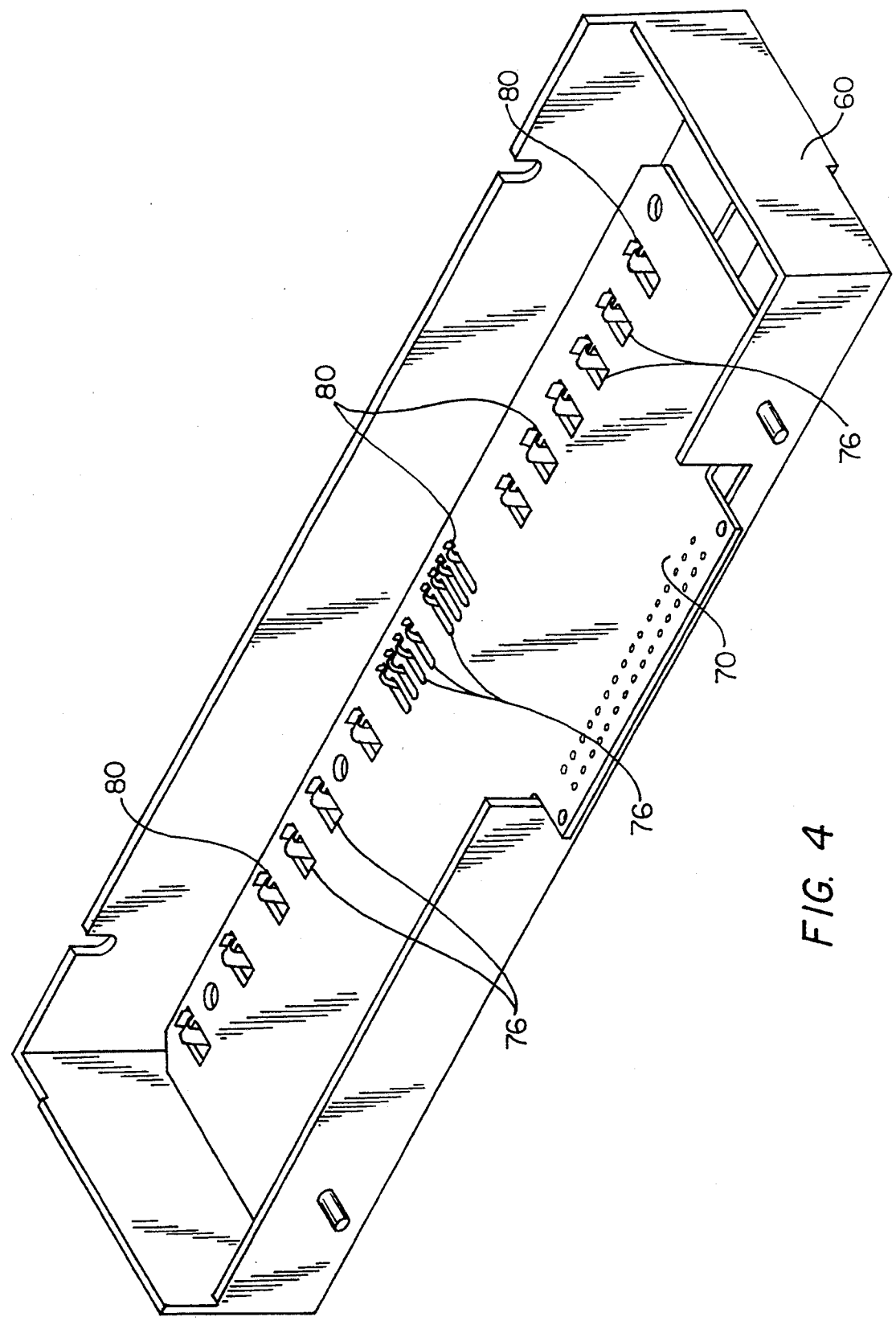
FIG. 4 is the perspective view of the housing of FIG. 3 having a printed circuit board installed therein.
Figure 5:
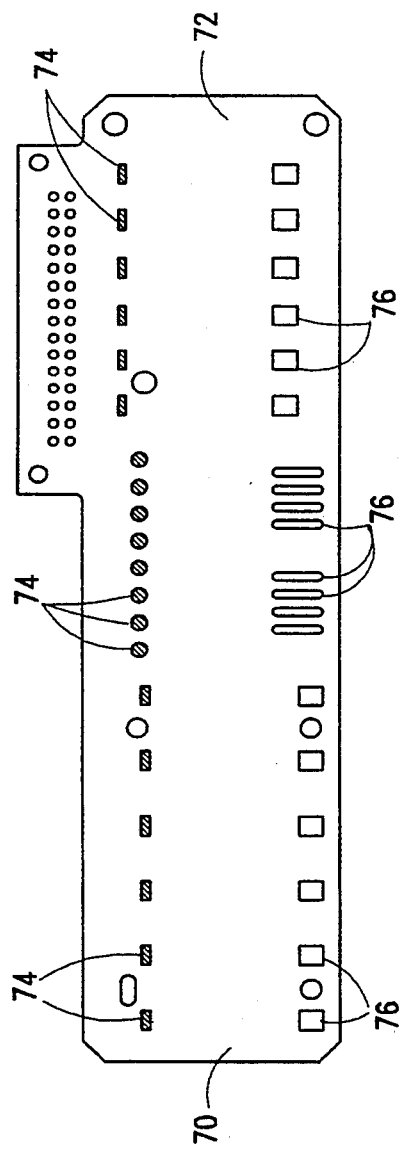
FIG. 5 is a plan view of a bottom surface of the printed circuit board of FIG. 4.

Once the contact stampings 20 are in place, a printed circuit board 70 is installed within the housing 60, as illustrated in FIG. 4. The printed circuit board 70 itself is best viewed in FIGS. 5 and 6, wherein printed circuit traces and discrete components have been omitted for the sake of clarity. With reference first to FIG. 5, a printed circuit board bottom surface 72 has input signal contacts 74 which correspond to the contact stampings 20 disposed within the housing 60 (see FIG. 3). When the printed circuit board 70 is installed within the housing 60, raised portions 78 of the contact stampings 20 are electrically and mechanically connected with the printed circuit board input signal contacts 74, which in turn are electrically connected to an input to the high impedance front-end circuitry 22 which may be mounted on the board 70 as in zone 71 (see FIG. 6) or externally, which could include access through a computer.

Figure 6:
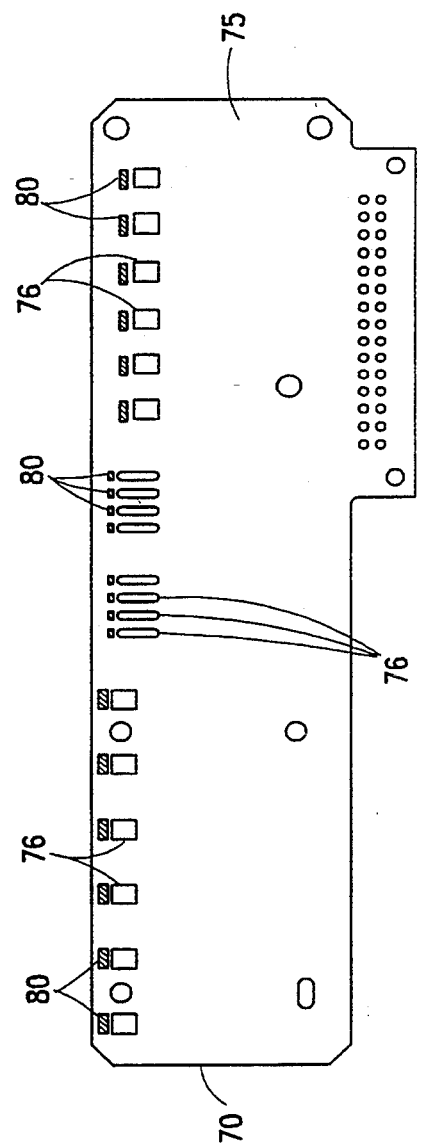
FIG. 6 is a plan view of a top surface of the printed circuit board of FIG. 4.

The printed circuit board 70 also has terminus apertures 76 through which the remote portion terminus 34 of the contact stamping remote portion 30 extends when the printed circuit board 70 is installed within the housing 60. As viewed in FIG. 6, illustrating a circuit board top surface 75, proximate each terminal orifice 76 is a respective diagnostic signal contact 80 electrically connected with the diagnostic circuitry 26, also typically on the board 70, or external.

Figure 7A:
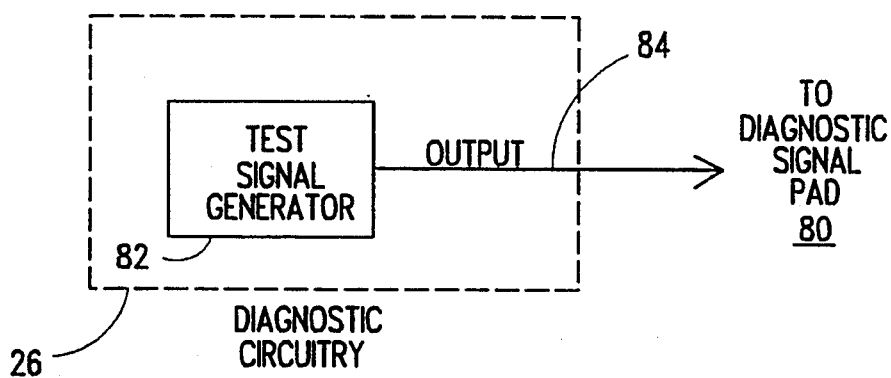
FIG. 7a is a schematic view of analyzer diagnostic circuitry according to the present invention.
Figure 7B:
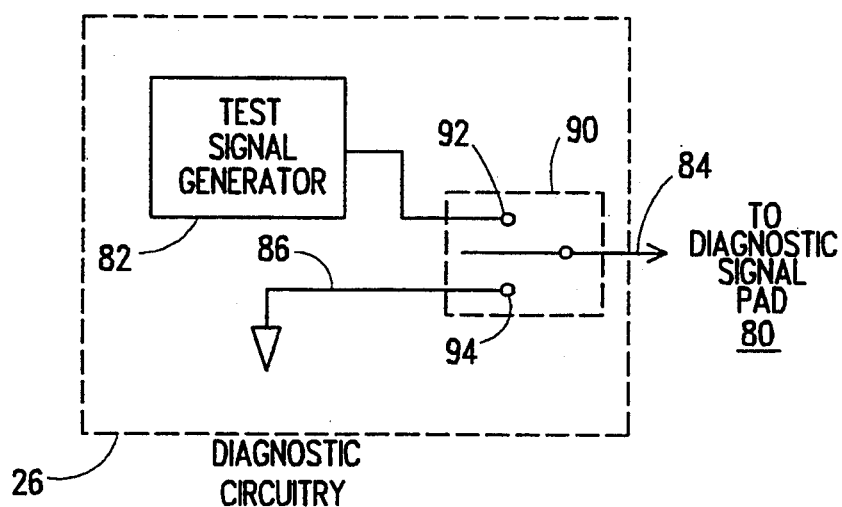
FIG. 7b is a schematic view of a further embodiment of analyzer diagnostic circuitry according to the present invention.

As shown in FIG. 7a, the diagnostic signal contact 80 may communicate directly with an output 84 of a test signal generator 82 which provides both test signals and a path to ground. In an alternative embodiment, as shown in FIG. 7b, the diagnostic signal contact 80 may communicate with the output of a switch 90, the switch 90 having inputs 92, 94 from the test signal generator 82 and from a path to ground 86.

The input signal contacts 74 and the diagnostic signal contacts 80 are typically formed of gold. The contact stampings 20 are typically manufactured of phosphor/bronze with a gold plating. Providing stampings and contacts of the same or similar material minimizes any thermocouple effects which may be present with dissimilar materials.

Figure 8A:
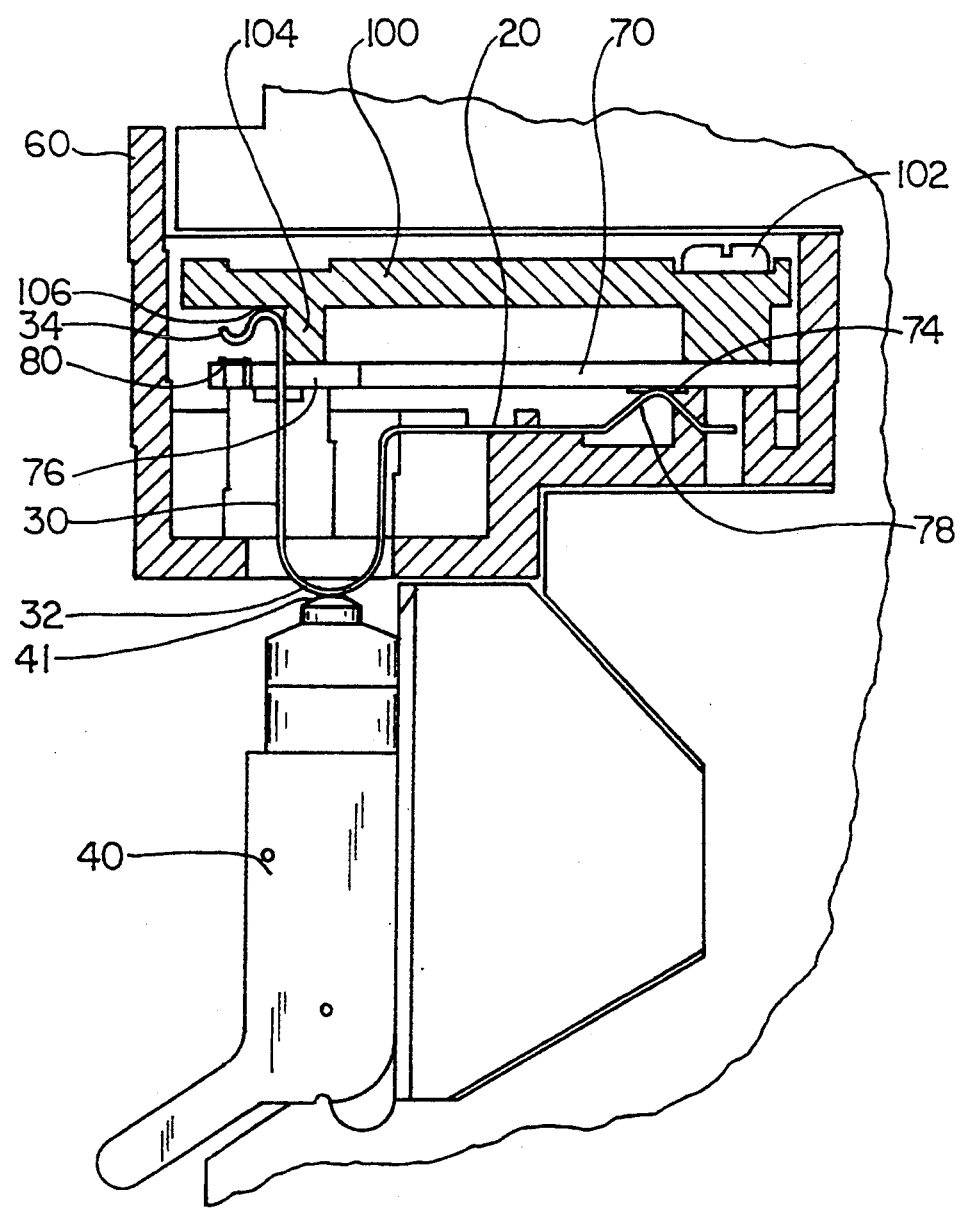
FIG. 8a is a side, sectional view of the analyzer of FIG. 2 showing a sensor installed.
Figure 8B:
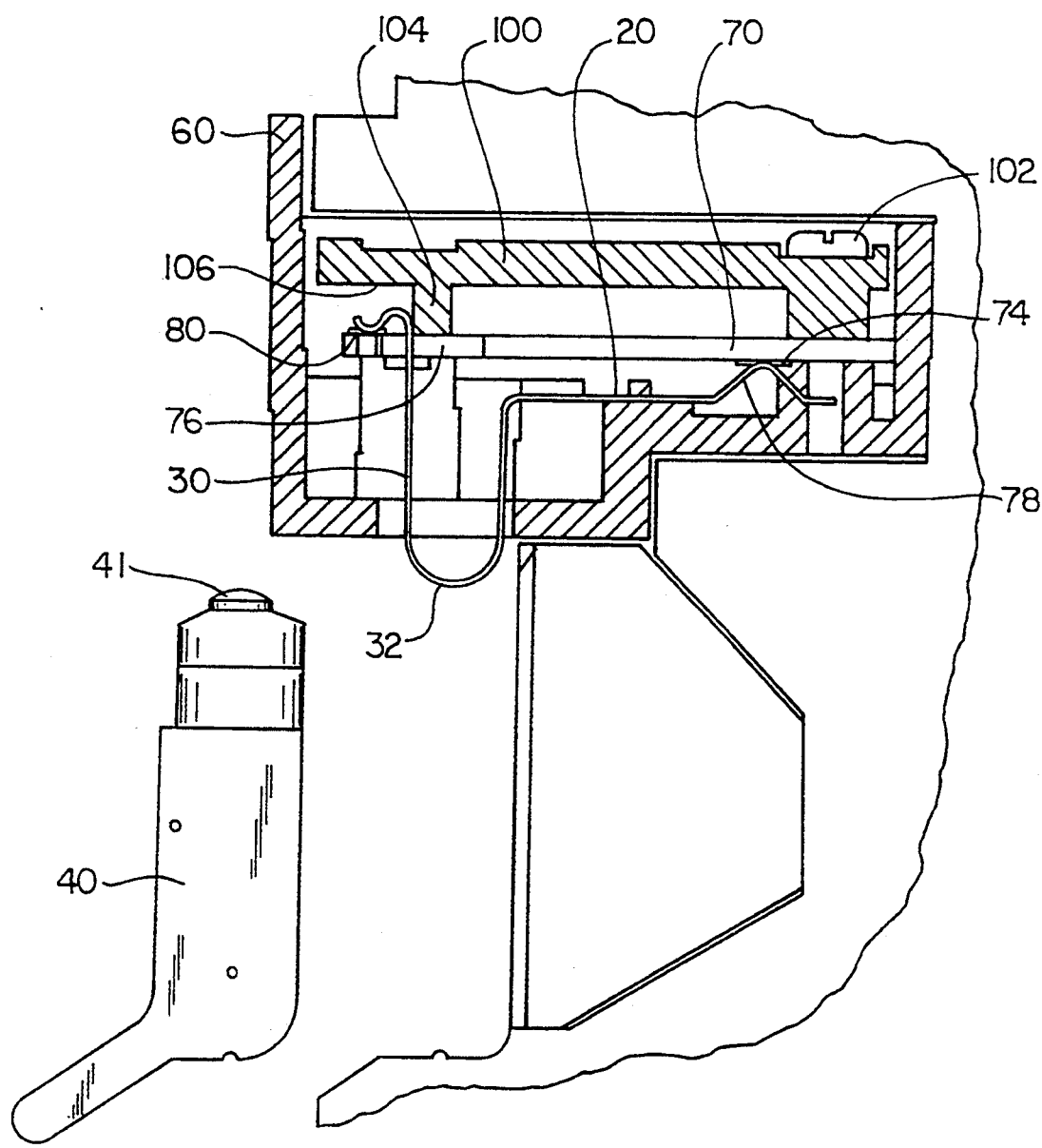
FIG. 8b is the side, sectional view of FIG. 8a showing a sensor removed.
Figure 8C:
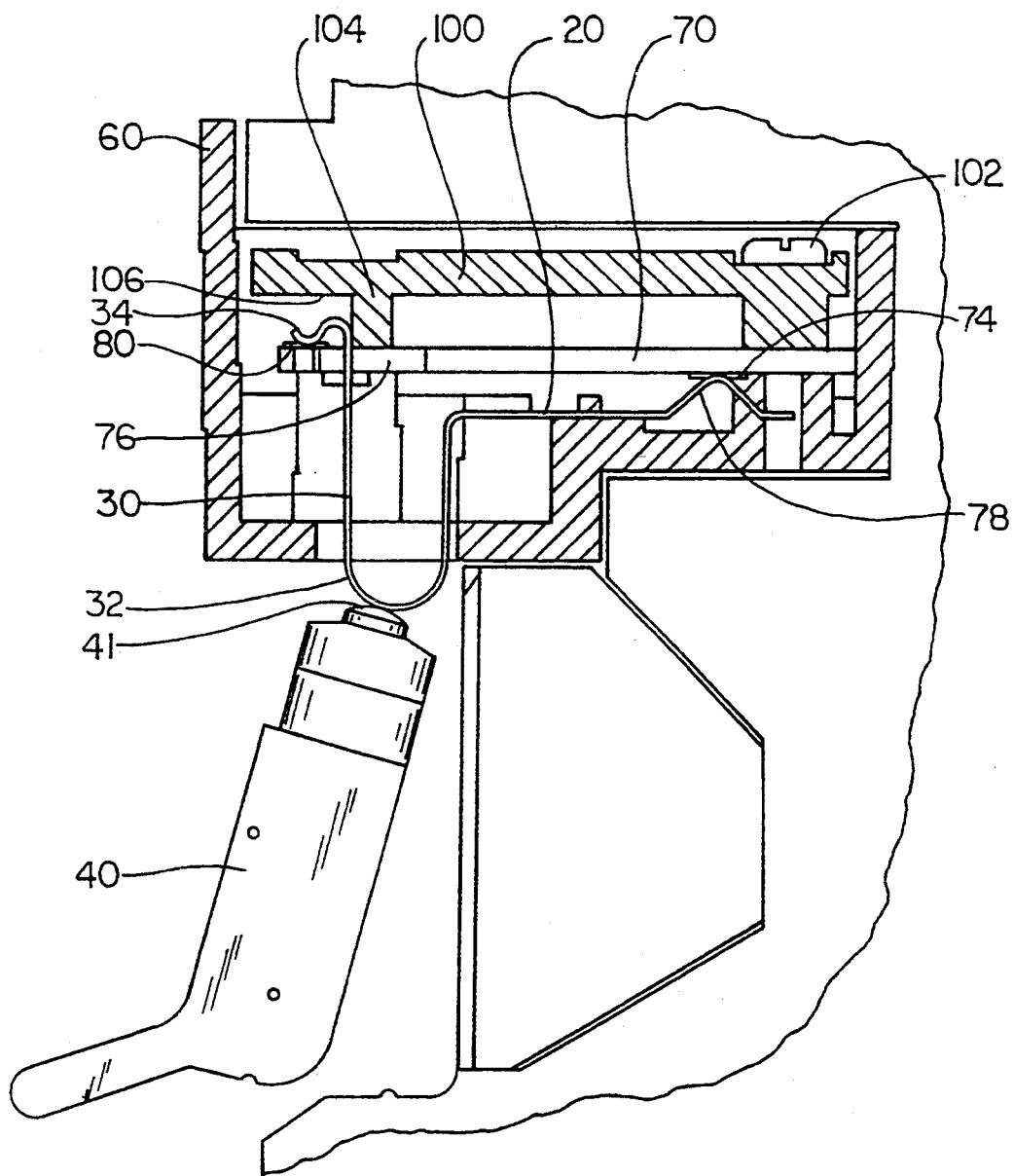
FIG. 8c is the side, sectional view of FIG. 8a showing a sensor partially installed.

The relative positions of analyzer elements with a sensor 40 installed and with a sensor 40 removed are best illustrated in FIGS. 8a, 8b and 8c. In FIG. 8a, a cover 100 is shown in place, securing the printed circuit board 70 within the housing 60 by way of screws 102, though other means for attaching the cover are employable. The cover 100 has projections 104, each disposed proximate a terminus aperture 76, diagnostic signal pad 80, and remote portion terminus 34. With the sensor 40 installed, pressure is exerted by the sensor contact 41 against the arcuate portion 32 of the remote portion 30, driving the associated remote portion terminus 34 away from the diagnostic signal contact 80, against a projection 104 and interrupting electrical connection with the diagnostic circuitry 26.

Without the cover projection 104, the remote portion terminus 34 would describe an arc as the remote portion 30 is driven upwards by the sensor contact 41 and as the sensor contact 41 is disengaged. As a result, without the cover projection 104, the remote portion terminus 34 could rest against an edge of the terminus aperture 76 when the sensor 40 is removed instead of returning to the diagnostic signal contact 80. With the cover 100 in place, the remote portion terminus 34 is guided upwards against the cover projection 104. The cover 100 also provides a stop 106 for limiting the upward travel of the remote portion 30 to prevent over-bending of the contact 20.

In FIG. 8b, the sensor 40 has been removed, allowing the remote portion terminus 34 to return to physical and electrical connection with the diagnostic signal contact 80. It is in this position that diagnostic signals can be conveyed to the analyzer processing electronics via the contact stamping 20.

As shown in FIG. 8c, as a sensor contact 41 is initially brought into contact with the arcuate portion 32 of the contact stamping remote portion 30, electrical continuity is established between the sensor contact 41, the contact stamping 20, and the diagnostic circuitry 26 via the diagnostic signal contact 80. As described with respect to FIGS. 7a and 7b, the ground path can be provided either through the output of a low impedance voltage source acting as a diagnostic signal generator 82, or through a discrete path to ground 86.

Also visible in FIGS. 8a, 8b, and 8c is the electrical and physical connection between the raised portions 78 of the contact stamping 20 and the input signal contact 74 disposed on the bottom surface 72 of the printed circuit board 70.

Although the invention has been shown and described with respect to an illustrative embodiment thereof, it should be understood by those skilled in the art that the foregoing and various other changes, omissions and additions in the form and detail thereof may be made therein without departing from the spirit and scope of the invention.

I claim:

1. An electrochemical/gas analyzer having plural installable constituent sensors and providing diagnostic capability and electrostatic discharge protection, comprising:
   a housing;
   a mounting board disposed within said housing; and
   a plurality of contact stampings captured between said board and housing and electrically contacting input signal circuitry, each of said plurality of contact stampings further comprising a first portion in interruptable electrical communication with diagnostic circuitry and a second portion for receiving a sensor contact during sensor installation to provide electrical connection between said sensor and said input signal circuitry while maintaining connection to said diagnostic circuitry and to interrupt connection to said diagnostic circuitry when said sensor is fully installed.

2. The electrochemical/gas analyzer according to claim 1, wherein said housing has a first side, said first side comprising a sensor mating face and a contact stamping retention face, and having a plurality of housing apertures disposed therein through which said second portion projects.

3. The electrochemical/gas analyzer according to claim 2, wherein said plurality of contact stampings are secured against said contact stamping retention face.

4. The electrochemical/gas analyzer according to claim 3, wherein at least one retention member retains said plurality of contact stampings against said contact stamping retention face.

5. The electrochemical/gas analyzer according to claim 4, wherein said at least one retention member is ultrasonically welded to said contact stamping retention face.

6. The electrochemical/gas analyzer according to claim 2, wherein said second portion comprises an arcuate portion, said arcuate portion disposed through a respective one of said plurality of housing apertures.

7. The electrochemical/gas analyzer according to claim 6, wherein said mounting board comprises:
   a first surface,
   an opposite second surface,
   a plurality of terminus apertures disposed through said mounting board, and
   a plurality of diagnostic signal contacts, each proximate a respective one of said plurality of terminus apertures, said diagnostic signal contacts in electrical communication with said diagnostic circuitry.

8. The electrochemical/gas analyzer according to claim 7, wherein said first portion further comprises a remote portion terminus, each said remote portion terminus protruding through a respective one of said plurality of terminus apertures and disposed in interruptable electrical connection with a respective one of a plurality of diagnostic signal contacts on said mounting board.

9. The electrochemical/gas analyzer according to claim 8, further comprising a sensor installation and retention surface proximate said first housing side for installing and retaining said sensor in a first partially inserted sensor position electrically connecting a sensor contact to said arcuate portion and maintaining said remote portion terminus in interruptable electrical connection with said diagnostic signal contact, thereby electrically connecting said diagnostic circuitry, said sensor, and said input signal circuitry.

10. The electrochemical/gas analyzer according to claim 9, further comprising said installation and retention surface for installing and retaining said sensor in a fully installed sensor position in which said sensor contact urges said remote portion terminus off said diagnostic signal contact, thereby electrically connecting said sensor and said input signal circuitry to the exclusion of said diagnostic contact.

11. The electrochemical/gas analyzer according to claim 7, wherein said diagnostic circuitry comprises a voltage or current test signal generation means, a ground path, and a diagnostic selection switch.

12. The electrochemical/gas analyzer according to claim 11, wherein said diagnostic selection switch has a first input electrically connected to said voltage or current test signal generation means, a second input electrically connected to said ground path, and an output electrically connected to said diagnostic signal contact.

13. The electrochemical/gas analyzer according to claim 1, wherein a plurality of input signal contacts electrically connected with said input signal circuitry are disposed on a first surface of said mounting board.

14. The electrochemical/gas analyzer according to claim 13, wherein said plurality of input signal contacts are in electrical communication with said plurality of contact stampings through non-interruptible contacts on said mounting board.

15. The electrochemical/gas analyzer according to claim 1, wherein said board has disposed thereon said input signal circuitry and said diagnostic circuitry.

16. A blood gas analyzer having plural installable constituent sensors and providing diagnostic capability and electrostatic discharge protection, comprising:
   a housing;
   a mounting board, said board disposed within said housing and comprising:
   signal processing circuitry, said signal processing circuitry receiving inputs from a plurality of input signal contacts, and
   diagnostic circuitry, said diagnostic circuitry providing inputs to a plurality of diagnostic signal contacts; and
   a plurality of contact stampings each having an input interface portion electrically connected to a respective one of said plurality of input signal contacts, each of said plurality of contact stampings further having a remote portion in interruptable electrical connection with a respective one of said plurality of diagnostic signal contacts.

17. The analyzer according to claim 16, wherein an installed analyzer mode comprises a sensor fully installed against said housing,
   wherein said sensor interrupts electrical connection between a respective remote portion and said diagnostic circuitry, and electrically connects said sensor and said signal processing circuitry.

18. The analyzer according to claim 16, wherein a discharge analyzer mode comprises a sensor partially installed against said housing,
   wherein a sensor contact is electrically connected to a respective one of said contact stamping remote portions, said respective remote portion electrically connected to said diagnostic circuitry, and
   said contact stamping electrically connecting said sensor, said diagnostic circuitry, and said signal processing circuitry.

19. The analyzer according to claim 16, wherein a diagnostic analyzer mode comprises a sensor removed from said housing,
   wherein a respective one of said remote portions is electrically connected to said diagnostic circuitry, and
   said contact stamping electrically connecting said diagnostic circuitry and said signal processing circuitry.

20. The analyzer according to claim 16, wherein said diagnostic circuitry comprises voltage or current test signal generation means, a ground path, and a test switch, said test switch providing a diagnostic circuitry output signal to each of said plurality of diagnostic signal contacts.

21. The analyzer according to claim 20, wherein said test switch comprises a first input electrically connected to said voltage or current test signal generation means, a second input electrically connected to said ground path, and an output electrically connected to said plurality of diagnostics signal contacts.

* * * * *